(12) United States Patent
Helson

(10) Patent No.: US 9,170,257 B2
(45) Date of Patent: Oct. 27, 2015

(54) METHOD AND SYSTEM FOR MEASURING THE PHARMACOKINETICS OF LIPOSOMAL CURCUMIN AND ITS METABOLITE TETRAHYDROCURCUMIN

(71) Applicant: SignPath Pharma Inc., Quakertown, PA (US)

(72) Inventor: Lawrence Helson, Quakertown, PA (US)

(73) Assignee: SIGNPATH PHARMA INC., Quakertown, PA (US)

( * ) Notice: Subject to any disclaimer, the term of this patent is extended or adjusted under 35 U.S.C. 154(b) by 0 days.

(21) Appl. No.: 13/918,112

(22) Filed: Jun. 14, 2013

(65) Prior Publication Data

US 2013/0337488 A1 Dec. 19, 2013

Related U.S. Application Data

(60) Provisional application No. 61/659,660, filed on Jun. 14, 2012.

(51) Int. Cl.
*G01N 33/50* (2006.01)
*G01N 33/84* (2006.01)

(52) U.S. Cl.
CPC ............ *G01N 33/5091* (2013.01); *G01N 33/50* (2013.01); *G01N 33/84* (2013.01)

(58) Field of Classification Search
CPC . A61K 31/12; A61K 31/122; A61K 36/9066; A61K 8/97; A61K 9/127; A61K 2121/00; A61Q 19/08; B82Y 5/00; G01N 33/487; G01N 33/49; G01N 33/15
See application file for complete search history.

(56) References Cited

U.S. PATENT DOCUMENTS

| | | | |
|---|---|---|---|
| 5,679,864 A | 10/1997 | Krackov et al. | |
| 7,060,733 B2 | 6/2006 | Pandol et al. | |
| 7,067,159 B2 | 6/2006 | Newmark et al. | |
| 8,153,172 B2 | 4/2012 | Antony | |
| 2008/0138400 A1* | 6/2008 | Kurzrock et al. | 424/450 |
| 2009/0317387 A1* | 12/2009 | Paton et al. | 424/133.1 |
| 2009/0324703 A1 | 12/2009 | Frautschy et al. | |
| 2011/0287085 A1 | 11/2011 | Kurzrock et al. | |

FOREIGN PATENT DOCUMENTS

JP H10-191927 A * 7/1998 ............... A23K 1/16

OTHER PUBLICATIONS

Whitten, Kenneth et al. The Common Ion Effect and Buffer Solutions. Chapter 19-1. In: Chemistry [online] Copyright 2013.Cengage Learning. Independence, KY. [retrieved on Jan. 30, 2014]. Retrieved from the Internet: <URL: http://books.google.com/books?id=XQiu__E72llkC&dq=Strong+acids+are+not+buffers&source=gbs__navlinks__s> p. 750.*
English translation.Takagaki, R. et al. 1998. Method for stabilizing curcuminoid and stabilized curcuminoid compound. Japanese Patent Application Publication No. JP 10191927 A, p. 1-11. specif pp. 4-5.*
Ireson, C. et al. 2001. Characterization of Metabolites of the Chemopreventive Agent Curcumin in Human and Rat Hepatocytes and in the Rat in vivo, and evaluation of their ability to inhibit Phorbol Ester-induced Prostaglandin E2 Production. Cancer Research 61:1058-1064. specif. pp. 1059-1060, 1062.*
Xie, Y. et al. 2007. Combinative method using HPLC quantitative and qualitative analyses for quality consistency assessment of a herbal medicinal preparation. Journal of Pharmaceutical and Biomedical Analysis 43:204-212. specif. pp. 205, 207-208.*
May et al. 2005. Detection and quantitation of curcumin in mouse lung cultures by matrix-assisted laser desorption ionization time of flight mass spectrometry. Analytical Biochemistry 337: 62-69. specif. pp. 62, 63.*
Wang, Y-J. et al. 1997. Stability of curcumin in buffer solutions and characterization of its degradation products. Journal of Pharmaceutical and Biomedical Analysis 15: 1867-1876. specif. pp. 1867, 1869, 1870, 1872.*
Oetari, S. et al. 1996. Effects of curcumin on cytochrome P450 and glutathione S-transferase activities in rat liver. Biochemical and Pharmacology 51: 39-45. specif. pp. 41, 42.*
English translation. Takagaki, R. et al. 1998. Method for stabilizing curcuminoid and stabilized curcuminoid compound. Japanese Patent Application Publication No. JP 10191927 A, pp. 1-11; specif. pp. 4, 5.*
Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Helson, et al., "Infusion pharmacokinetics of lipocure (liposomal curcumin) and its metabolite tetrahydrocurcumin in beagle dogs," Anticancer Research, Oct. 2012, vol. 32, No. 10, pp. 4365-4370.
Leung, et al., "Effective stablization of curcumin by association to plasma proteins: human serum albumin and fibronogen," Langmuir, 2009, vol. 25, Issue 10, pp. 5773-5777.
Tonnesen, et al., "Studies on curcumin and curcuminoids," Zeitschrift fur Lebensmittel-Untersuchung und Forschung, May 1985, vol. 180, pp. 402-404.
International Search Report and Written Opinion of PCT/US2013/045898 dated Sep. 6, 2013.

* cited by examiner

*Primary Examiner* — John S Brusca
*Assistant Examiner* — Sharon M Papciak
(74) *Attorney, Agent, or Firm* — Edwin Flores; Chainey P. Singleton; Chalker Flores, LLP

(57) ABSTRACT

The present invention includes a stabilized curcumin composition. The composition includes a curcumin composition and a phosphate composition, wherein the phosphate composition is non-buffering and is provided in an amount sufficient to stabilize and/or prevent the degradation of curcumin and/or a curcuminoid in a biological sample.

17 Claims, 4 Drawing Sheets

METHOD AND SYSTEM FOR MEASURING THE PHARMACOKINETICS OF LIPOSOMAL CURCUMIN AND ITS METABOLITE TETRAHYDROCURCUMIN

CROSS-REFERENCE TO RELATED APPLICATIONS

This application claims priority to U.S. Provisional Application Ser. No. 61/659,660, filed Jun. 14, 2012, the entire contents of which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates generally to compositions and methods for stabilizing curcumin and tetrahydrocurcumin (THC) and in particular, to compositions and methods for stabilizing curcumin and THC in plasma and bile against degradation occurring during analytical processes by lowering the pH with phosphoric acid.

BACKGROUND OF THE INVENTION

Without limiting the scope of the invention, its background is described in connection with methods of stabilizing curcumin and THC in plasma and bile against degradation occurring during analytical processes. Curcumin is the major yellow pigment of turmeric, derived from the rhizome of the herb *Curcuma longa* Linn, and has traditionally been used as a treatment for inflammation, skin wounds, and tumors. In addition, preclinical animal models, curcumin has shown cancer chemo preventive, antineoplastic and anti-inflammatory properties. Curcumin [1,7-bis(4-hydroxy-3-methoxyphenyl)-1,6-heptadiene-3,5-dione] has the structure below:

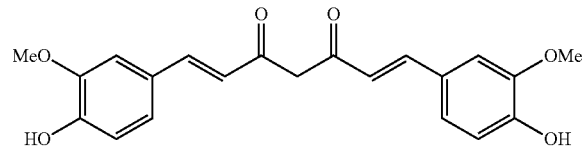 [SMILES: COc1cc(/C=C/C(=O)CC(=O)/C=C/c2ccc(O)c(OC)c2)ccc1O]

Curcumin acts as a scavenger of hydroxyl radical, superoxide anion and singlet oxygen and other oxygen species. Curcumin plays a role in cellular signal induction pathways pertinent to growth, differentiation and malignant transformations, including inhibiting protein kinases, c-Jun/AP-1 activation, prostaglandin biosynthesis, and may play a role in the activation of the transcription factor NF-κB. However, it has been thought that the bioavailability of curcumin in animals remains low with a poor bioavailability which may be related to its inadequate absorption and fast metabolism. Indirect evidence suggests that curcumin is metabolized in the intestinal tract where curcumin undergoes metabolic O-conjugation to curcumin glucuronide and curcumin sulfate and bioreduction to THC, hexahydrocurcumin and hexahydrocurcuminol. Much of this is confirmed through examination and analysis of curcumin present in samples (e.g., tissue extracts) before and after treatment. In studies it has been shown that perorally administered curcumin has poor bioavailability and only low or non-measurable blood levels were observed. Others have administered piperine along with curcumin to enhance the bioavailability of curcumin; however, the level of enhancement was only modest and no curcumin could be detected after 3 hours even when supplemented with piperine.

U.S. Pat. No. 8,153,172, entitled "Composition to Enhance the Bioavailability of Curcumin," discloses a composition having a curcuminoid and an essential oil of turmeric. A composition having a curcuminoid and an essential oil of turmeric, wherein the essential oil is present in an amount sufficient to cause an enhancement of bioavailability of curcumin when the composition is administered to a human as compared to bioavailability of curcumin obtained upon administration of a composition prepared without adding essential oil to the curcuminoid. A method to prepare a composition having a curcuminoid and an essential oil of turmeric.

U.S. Pat. No. 7,067,159, entitled "Methods for Treating Prostate Cancer with Herbal Compositions," discloses methods for treating prostate cancer, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

U.S. Pat. No. 7,060,733, entitled "Methods for Treating Pancreatitis with Curcumin Compounds and Inhibitors of Reactive Oxygen Species," discloses methods of treating, preventing, modulating, attenuating, or inhibiting a disease or a disorder associated with inflammation related to NF-κB activation in a subject which comprises administering to the subject at least one curcumin compound. Also disclosed are combination therapies comprising the administration of at least one curcumin compound and at least one ROS inhibitor. Pharmaceutical compositions and kits are also disclosed.

U.S. Pat. No. 5,679,864, entitled "Process for the Synthesis of Curcumin-Related Compounds," discloses a process for the synthesis of curcumin and curcumin-related compounds by reacting the enol form of a 2,4-diketone with a monocarbocyclic aldehyde in the presence of an organic amine catalyst. The reactants are dissolved in a highly polar, aprotic organic solvent. The curcumin-related product is recovered in crystalline form by precipitation from the reaction mass and solvent recrystallization.

SUMMARY OF THE INVENTION

The present invention provides a method of stabilizing curcumin and tetrahydrocurcumin in the plasma and bile against degradation occurring during analytical processes by lowering the pH with phosphoric acid. One embodiment of the present invention provides a method of determining a curcumin level in a biological sample by providing a biological sample comprising a curcuminoid composition and adding a strong acid, e.g., a phosphate composition, to the sample, wherein the phosphate composition is non-buffering and detecting the amount of curcuminoid in the sample, wherein the non-buffering strong acid reduces the degradation of the curcuminoid in the sample. The biological sample may be an in vitro sample and include an aqueous sample, a supernatant sample, a tears sample, a sputum sample, a blood sample or a bile sample. The curcuminoid composition may include curcumin and analogues and derivatives selected from curcumin; tetrahydrocurcumin; hexahydrocurcumin and hexahydrocurcuminol; curcumin glucuronide; and curcumin sulfate and the phosphate composition may include a phosphoric acid; an orthophosphoric acid; a phosphate salt; or a Na-phosphate. The curcuminoid composition may include a liposome, a phospholipid or a polymer composition to form an encapsulated curcuminoid composition and the liposome, the phospholipid or the polymer composition is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate; or wherein the polymer composition is selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof and have a size of about 10-900 nm.

One embodiment of the present invention provides a stabilized curcumin composition. The composition includes a curcumin composition and a phosphate composition, wherein the phosphate composition is non-buffering, wherein and wherein the non-buffering strong acid reduces the degradation of the curcuminoid in the sample. As a result the phosphate composition does not include an aqueous solution consisting of a mixture of a weak acid and its conjugate base or a weak base and its conjugate acid. The curcumin composition may be a curcumin composition, a modified curcumin composition or a product of a curcumin degradation, for example, the curcumin composition may be selected from curcumin; tetrahydrocurcumin; hexahydrocurcuminol; curcumin glucuronide; curcumin sulfate or other related products. In addition the curcumin composition may be a mixture of the 2 or more modified curcumin compositions, a product of a curcumin degradation, modified curcumin or synthetic curcumin compositions. The phosphate composition is a phosphate containing composition that is non-buffering and as a result is not mixture of a weak acid and its conjugate base or a weak base and its conjugate acid, e.g., not a PBS. In one embodiment of the present invention, the phosphate composition is a phosphoric acid. In other embodiments the phosphate composition can be an orthophosphoric acid; a phosphate salt; a Na-phosphate; a K-phosphate; or other counter ion phosphate. In other embodiments the phosphate composition can be a mixture of phosphate compositions as long as the final composition is not a buffer, i.e., not mixture of a weak acid and its conjugate base or a weak base and its conjugate acid. The stabilized curcumin can further comprising a liposome to form a liposomal curcumin composition and can be in any common dosage form known to the skilled artisan including infusion nanoparticle, tablet, capsule, liquid and the like.

One embodiment of the present invention includes a method of analyzing a curcumin sample by providing a sample comprising a curcumin composition and adding a phosphate composition to the sample, wherein the phosphate composition is non buffering and at least one of stabilizes or reduced the degradation of the curcumin in the sample. The method can then include the step of analyzing at least one property of the sample and in some cases the sample is an aqueous sample, a blood sample or a bile sample. As a result the phosphate composition does not include an aqueous solution consisting of a mixture of a weak acid and its conjugate base or a weak base and its conjugate acid. The curcumin composition may be a curcumin composition, a modified curcumin composition or a product of a curcumin degradation, for example, the curcumin composition may be selected from curcumin; tetrahydrocurcumin; hexahydrocurcuminol; curcumin glucuronide; curcumin sulfate or other related products. In addition the curcumin composition may be a mixture of the 2 or more modified curcumin compositions, a product of a curcumin degradation, modified curcumin or synthetic curcumin compositions. The phosphate composition is a phosphate containing composition that is non-buffering and as a result is not mixture of a weak acid and its conjugate base or a weak base and its conjugate acid, e.g., not a PBS. In one embodiment of the present invention, the phosphate composition is a phosphoric acid. In other embodiments the phosphate composition can be an orthophosphoric acid; a phosphate salt; a Na-phosphate; a K-phosphate; or other counter ion phosphate. In other embodiments, the phosphate composition can be a mixture of phosphate compositions as long as the final composition is not a buffer, i.e., not mixture of a weak acid and its conjugate base or a weak base and its conjugate acid.

One embodiment of the present invention provides a method of stabilizing a curcumin or tetrahydrocurcumin sample by providing a sample comprising curcumin composition and adding a phosphate composition to the sample, wherein the phosphate composition is non buffering and at least one of stabilizes or reduced the degradation of the curcumin in the sample. As a result, the phosphate composition does not include an aqueous solution consisting of a mixture of a weak acid and its conjugate base or a weak base and its conjugate acid. The curcumin composition may be a curcumin composition, a modified curcumin composition or a product of a curcumin degradation; for example, the curcumin composition may be selected from curcumin, tetrahydrocurcumin, hexahydrocurcuminol, curcumin glucuronide, curcumin sulfate or other related products. In addition, the curcumin composition may be a mixture of the 2 or more modified curcumin compositions, a product of a curcumin degradation, modified curcumin or synthetic curcumin compositions. The phosphate composition is a phosphate containing composition that is non-buffering and as a result is not a mixture of a weak acid and its conjugate base or a weak base and its conjugate acid, e.g., not a PBS. In one embodiment of the present invention, the phosphate composition is a phosphoric acid. In other embodiments the phosphate composition can be an orthophosphoric acid, a phosphate salt, a Na-phosphate, a K-phosphate, or other counter ion phosphate. In other embodiments, the phosphate composition can be a mixture of phosphate compositions as long as the final composition is not a buffer, i.e., not a mixture of a weak acid and its conjugate base or a weak base and its conjugate acid.

One embodiment of the present invention provides a curcumin diagnostic kit including a non-buffering phosphate composition and a set of instructions for stabilizing a curcumin sample using the non-buffering phosphate composition, wherein the amount of a non-buffering phosphate composition sufficient to stabilize a curcuminoid in a biological sample, and wherein the non-buffering phosphate composition comprises a phosphoric acid; an orthophosphoric acid; a phosphate salt; or a Na-phosphate to stabilize Curcumin; tetrahydrocurcumin; hexahydrocurcumin and hexahydrocurcuminol; curcumin glucuronide; and curcumin sulfate. As a result the phosphate composition does not include an aqueous solution consisting of a mixture of a weak acid and its conjugate base or a weak base and its conjugate acid.

Another embodiment of the present invention provides a method of stabilizing a curcumin composition in plasma sample or a bile sample against degradation during an analytical processes by providing a sample comprising a curcumin composition, wherein the sample is a bile sample or a blood sample and the curcumin composition is selected from Curcumin; tetrahydrocurcumin; hexahydrocurcumin and hexahydrocurcuminol; curcumin glucuronide; and curcumin sulfate and adding a phosphate composition to the sample, wherein the amount of a non-buffering phosphate composition is sufficient to stabilize a curcuminoid in a biological sample. As a result the phosphate composition does not include an aqueous solution consisting of a mixture of a weak acid and its conjugate base or a weak base and its conjugate acid. The curcumin composition may be a curcumin composition, a modified curcumin composition or a product of a curcumin degradation, for example, the curcumin composition may be selected from curcumin; tetrahydrocurcumin; hexahydrocurcuminol; curcumin glucuronide; curcumin sulfate or other related products. In addition the curcumin composition may be a mixture of the 2 or more modified curcumin compositions, a product of a curcumin degradation, modified curcumin or synthetic curcumin compositions. The phosphate composition is a phosphate containing composition that is non-buffering and as a result is not mixture of a weak acid and its conjugate base or a weak base and its conjugate acid, e.g., not a PBS. In one embodiment of the present invention, the phosphate composition is a phosphoric acid. In other embodiments the phosphate composition can be an orthophosphoric acid; a phosphate salt; a Na-phosphate; a K-phosphate; or other counter ion phosphate. In other embodiments the phosphate composition can be a mixture of phosphate compositions as long as the final composition is not a buffer, i.e., not mixture of a weak acid and its conjugate base or a weak base and its conjugate acid. The stabilized curcumin can further comprising a liposome to form a liposomal curcumin composition and can be in any common dosage form known to the skilled artisan including infusion nanoparticle, tablet, capsule, liquid and the like.

Another embodiment of the present invention provides a method of performing a clinical trial to evaluate a candidate drug comprising a curcumin or curcuminoid believed to be useful in treating a medical condition, the method comprising: (a) obtaining a first tissue samples prior to providing the candidate substance from tissue suspected from a set of patients; (b) administering the candidate drug to a first subset of the patients, and a placebo to a second subset of the patients; (c) repeating step (a) after the administration of the candidate drug or the placebo; and (d) obtaining a second tissue sample from the first and second set of patients and stabilizing the curcumin or curcuminoids in the second tissue samples by adding an effective amount of a non-buffering phosphate; and (e) determining of there is a statistically significant difference in the amount of curcumin or curcuminoids in the second tissue samples between the first and second subset of patients, wherein a statistically significant reduction indicates that the candidate drug is useful in treating said disease state.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
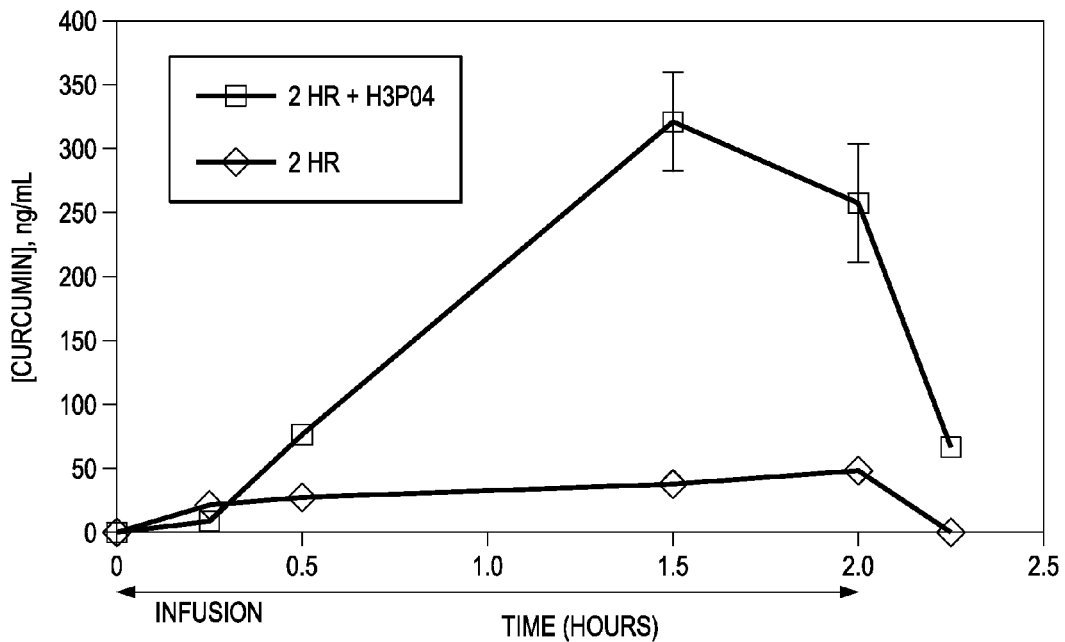
FIGS. 1A-1D are graphs of the plasma levels of curcumin and THC as a function of time after infusion.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "liposome" refers to a capsule wherein the wall or membrane thereof is formed of lipids, especially phospholipid, with the optional addition therewith of a sterol, especially cholesterol.

As used herein, the term "in vivo" refers to being inside the body. The term "in vitro" used as used in the present application is to be understood as indicating an operation carried out in a non-living system.

The terms "effective amount" or "therapeutically effective amount" described herein means the amount of the subject compound that will elicit the biological or medical response of a tissue, system, animal or human that is being sought by the researcher, veterinarian, medical doctor or other clinician.

The term "pharmaceutically acceptable" as used herein to describe a carrier, diluent or excipient must be compatible with the other ingredients of the formulation and not deleterious to the recipient thereof.

The term "curcumin" as used herein to describe (i) curcumin derivatives or combinations thereof dissolved or dispersed in an aqueous or a non-aqueous solvent with one or more optional related co-factors, proteins, antibodies, pain medications, and other pharmaceutically active agents dissolved, dispersed or suspended in the solvent, (ii) a suitable aqueous or non-aqueous dispersion medium, wherein the one or more spherical liposomes are dispersed in the dispersion medium, and (iii) one or more optional excipients, diluents, extended or controlled release agents, lubricants, preservatives or any combinations thereof.

The present invention provides the stabilization of curcumin and/or THC in plasma; however, the stabilization is more complicated than the acidification of plasma with $H_3PO_4$. For example, in Phase 1, human plasma samples were stabilized with the addition of Na-phosphate, however, the bench stability of both curcumin and THC was minimal and no curcumin and/or THC were detected after the samples sat on the bench at room temperature for a couple of hours. The addition of Na-phosphate stabilized the plasma, although not as efficient as with $H_3PO_4$. As a result, one embodiment of the present invention provides the stability of curcumin and THC in plasma by the addition of Na-phosphate. Another embodiment of the present invention provides the stability of curcumin and THC in plasma by the addition of O-Phosphoric acid. Another embodiment of the present invention provides the stability of curcumin and THC in plasma by the addition of Na-phosphate and O-Phosphoric acid. O-Phosphoric acid can be more easily incorporated in the plasma or body fluids. The phosphate molecule is essential for stabilizing the curcumin and THC, both the sodium phosphate and phosphoric acid can be used. In contrast, a phosphate buffer does not stabilize curcumin and THC in plasma. The phosphate buffer is not specific to which salt it is made from and can be made with either sodium or potassium phosphate (monobasic or dibasic) whereas sodium phosphate monobasic is specific as is orthophosphoric acid. The main purpose of adding the phosphate/phosphoric acid is to stabilize the curcumin and THC in the plasma. As we have seen the presence of the phosphoric acid in the plasma shows a higher concentration for the analytes. This stabilisation process may as well be achieved by using other phosphate salts known to the skilled artisan. The addition of $H_3PO_4$ leads to higher curcumin concentrations because of the shift in pH confirmation. For example, the pH of EDTA plasma is 7.95, which is a little higher than the pH of plasma without EDTA. After the addition of 50 µl 5% $H_3PO_4$ to 950 ml plasma the pH was 4.4. As curcumin is stable at pH values below 5.5 the addition of $H_3PO_4$ stabilizes curcumin in the plasma samples. Other embodiments may use other acidification agents (e.g. ACD, acidic citrate, etc.) and may also use anticoagulants. In addition, the urine tends to be more acidic with a pH of between 5 and 7; however, no stabilization was observed with $H_3PO_4$.

The present invention provides a method of stabilizing curcumin and THC in the plasma and bile against degradation occurring during analytical processes by lowering the pH with phosphoric acid. In one study of 4 dogs, 2 males and 2 females were infused with 10 mg/kg liposomal curcumin (LIPOCURC™) over 2 hours, and another 4 dogs, 2 males and 2 females were infused with 10 mg/kg liposomal curcumin (LIPOCURC™) over 8 hours. Plasma levels of curcumin and THC were obtained at necropsy 15 minutes following the infusion. THC levels were 6.3-9.6 fold higher than curcumin at both infusion rates suggesting a combination of a high rate of enzymatic curcumin metabolism and a comparatively slower rate of blood THC clearance. Compared to the 8 hour infusion, the 2 hour infusion levels of both curcumin and its metabolite THC were significantly higher. The plasma half lives of both compounds following the 2 hour infusion ranged from 0.4-0.7 hours, and was a consequence of both hepatic and renal clearance. However at higher plasma concentrations renal excretion predominates particularly with THC. Enhanced clearance rates were noted during the 8 hour infusions which prevented achieving a steady state. These observations suggest that for hematopoietic malignancies including leukemia, lymphoma, and bone marrow metastases, the 2 hour infusion may be advantageous based upon higher concentration profiles, and the unstimulated clearance rates.

The parenteral administration of liposomal curcumin (LIPOCURC™) with therapeutic intent poses several questions relating to deciding an optimal rate of administration for patients with neoplastic diseases. Options ranging from bolus intravenous injections to constant infusions are impacted by enzymatic metabolism, pH dependent degradation, renal and hepato-biliary excretion mechanisms. During pre-clinical toxicological evaluation in dogs, dose dependent hemolysis was noted following brief infusions of 20 mg/kg and greater curcumin content. Ten mg/kg doses infused over 2 hours were nontoxic. This same 2 hour infusion schedule was used in an ascending dose Phase 1 trial in normal human subjects where the highest intravenous dose administered (5 mg/kg) was without adverse reaction. To avoid toxicity from a too-high $C_{max}$ we used a two hour infusion, however in view of the unknown metabolic and elimination factors in dogs we compared 2 hour and 4 fold longer infusions (8 hours) to determine any advantages.

Plasma concentration data arising from the infusion of liposomal curcumin (LIPOCURC™) in 8 dogs (4 females and 4 males) of the Beagle breed were used. The results and analysis for the study are presented for intravenous infusion dosing of a total dose of 10 mg/kg infused over a period of either 2 or 8 hours. Plasma levels of curcumin and its metabolite, THC were measured at timed intervals post-dosing. All animals were euthanized and subject to necropsy 15 minutes post-infusion and samples of tissues, plasma, bile, and urine taken to determine, the tissue distribution and pharmacokinetics of curcumin and THC following two different rates of infusion and two different analyte preservation/stabilization methods, e.g., with and/or without phosphoric acid ($H_3PO_4$) and the plasma pharmacokinetics, urine and bile levels of curcumin and THC reviewed. A summary of the treatment groups is presented in Table 1 below.

TABLE 1

Summary of Treatment Groups

| Groups | Dose (mg/kg) | Concentration of Curcumin (mg/mL) | Infusion Rate mL/kg/hr | Duration of Infusion (hr) | Number of Beagle Dogs On Study[a] | |
|---|---|---|---|---|---|---|
| | | | | | M | F |
| Part A, Liposomal Curcumin | 10 | 0.5 | 10 | 2 | 2 | 2 |
| Part B, Liposomal Curcumin | 10 | 0.125 | 10 | 8 | 2 | 2 |

Liposomal curcumin (LIPOCURC™) was administered to 8 Beagle dogs by intravenous infusion over two hours (Part A) or eight hours (Part B). For the 2 hour infusion, blood samples were taken at predose and 0.25, 0.5, 1.5 and at 2 hours during infusion and at 15 minutes post-infusion. For the 8 hour infusion, blood samples were taken at predose and 0.25, 0.5, 1.5, 4, 4, 6 and at 8 hours during infusion and at 15 minutes post-infusion.

For all groups, plasma curcumin and THC were determined using a method developed by the Bioanalytical Department at Nucro-Technics [1]. Bioanalysis was performed on two sets of samples, one set that was treated with phosphoric acid and one set that was not treated with phosphoric acid. Phosphoric acid was used to treat one set of samples based on preliminary studies indicating that phosphate increased the stability of curcumin and THC in the tissue matrix. Values that were below the limit of quantification were assigned a value of 0.

As there were no consistent differences between the plasma levels of curcumin in male dogs or female dogs, the average plasma concentrations from male and female dogs were used to perform the PK analysis. Plasma concentration vs. time profiles were analyzed using (unless otherwise stated) the data from 4 dogs. Plasma profiles for the test articles are presented as the mean data±SE of 4 dogs. Average plasma concentrations were used to perform the PK analysis. Plasma concentration vs. time profiles were analyzed and the PK parameters estimated using WinNonlin Version 5.2.1 employing the intravenous infusion model with first order elimination. Unless stated otherwise, the plasma concentration-time profiles for the test articles are presented as the mean data±SE of 4 dogs.

Figure 1B:
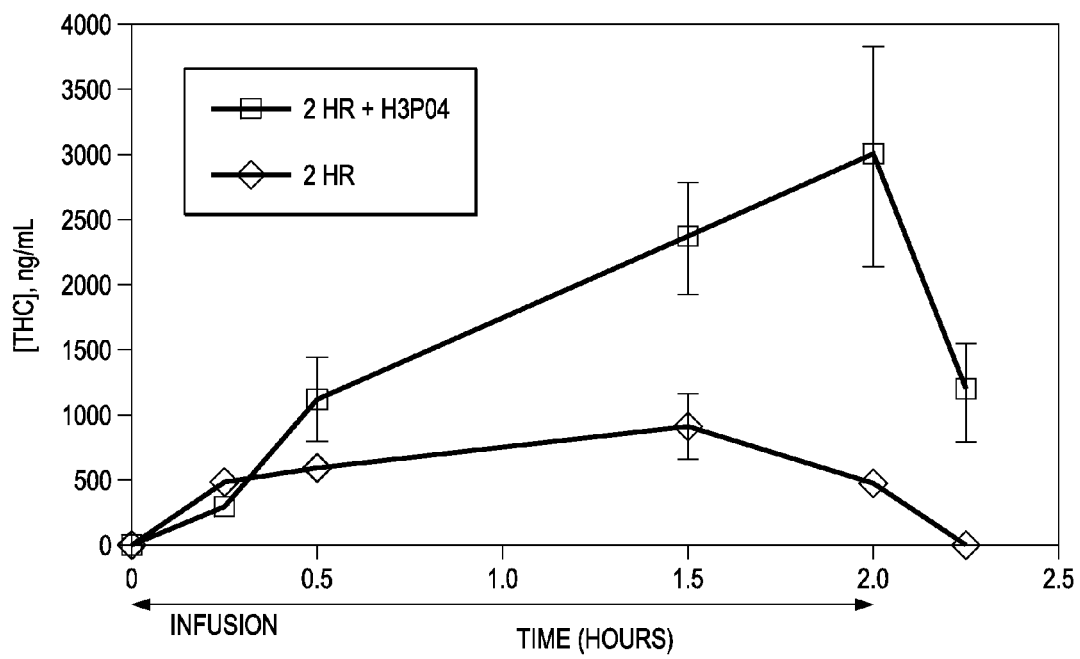
Figure 1C:
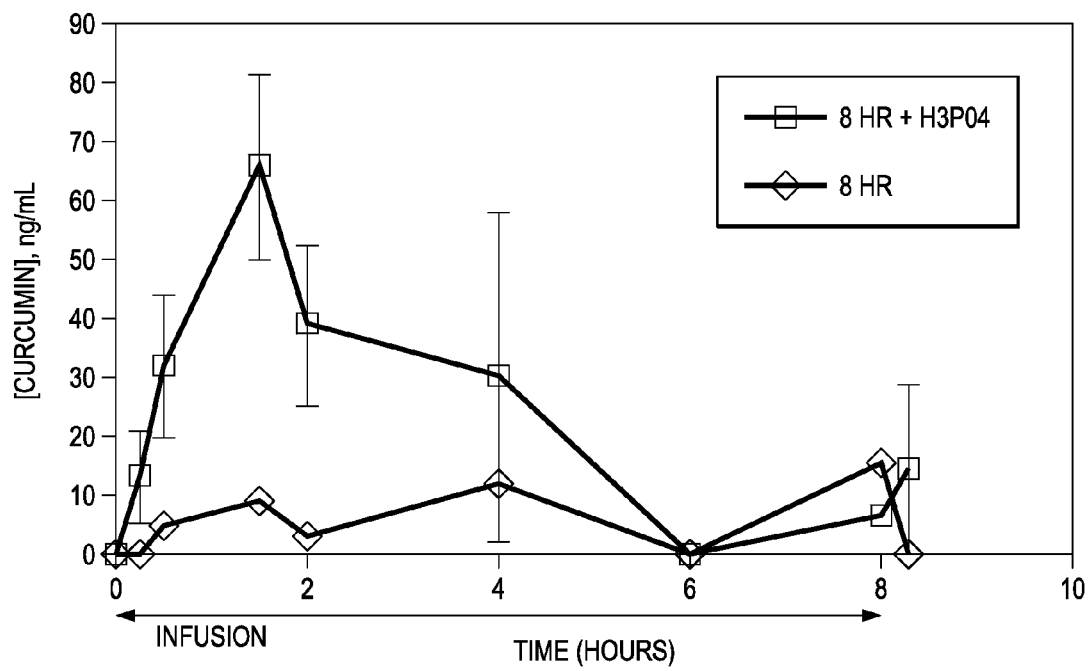
Figure 1D:
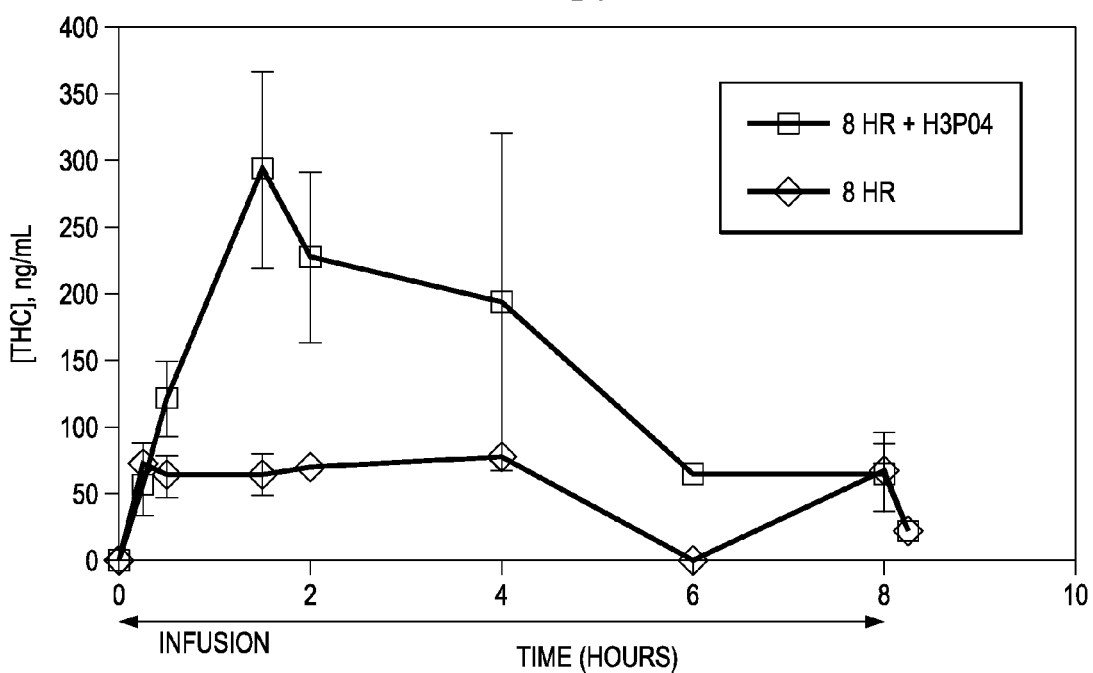

FIGS. 1A-1D are graphs of the plasma levels of curcumin as a function of time after infusion. FIG. 1A is a graph of the plasma level of curcumin following a 2 hour infusion of 5 mg/kg/hr of curcumin. FIG. 1B is a graph of the plasma level of curcumin following an 8 hour infusion of 1.25 mg/kg curcumin. FIG. 1C is a graph of the plasma level of THC following a 2 hour infusion of 5 mg/kg/hr curcumin. FIG. 1D is a graph of the plasma level of THC following an 8 hour infusion of 1.25 mg/kg/hr curcumin. Values are presented as the mean±standard error of 4 dogs.

The plasma levels and AUC of curcumin and THC following either 2 hours (high rate) or 8 hours (low rate) infusion were clearly higher in the presence of phosphoric acid (Tables 2 and 3), suggesting that phosphoric acid increased the stability of curcumin and THC in plasma samples.

Table 2 below is a table of the AUC of plasma concentration vs. time for curcumin and THC upon bioanalysis in the presence and absence of phosphoric acid. Phosphoric acid was added to the plasma samples in the form of phosphoric acid; $C_{max}$ represents the observed value and AUC is the area under the curve to 15 minutes post-infusion calculated using the linear trapezoidal rule.

| Infusion Time | AUC (ng/mL * hr) | | $C_{max}$ (ng/mL) | |
|---|---|---|---|---|
| | Curcumin | THC | Curcumin | THC |
| 2 hr | 65 | 1318 | 46 | 891 |
| 2 hr + phosphate | 394 | 3797 | 320 | 2983 |
| 8 hr | 52 | 411 | 15 | 77 |
| 8 hr + Phosphate | 187 | 1171 | 66 | 293 |

Table 3 below is a table of the plasma concentration vs. time for curcumin and THC upon bioanalysis in the presence and absence of phosphoric acid.

| Infusion Rate and Time | [Plasma], ng/mL | | [Plasma + PO₄], ng/mL | |
|---|---|---|---|---|
| | Curcumin | THC | Curcumin | THC |
| 5 mg/kg/hr | | | | |
| Pre-Dose | 0 ± 0 | 0 ± 0 | 0 ± 0 | 0 ± 0 |
| 15 min | 20 ± 2 | 483 ± 50 | 8 ± 3 | 284 ± 89 |
| 30 min | 25 ± 5 | 566 ± 77 | 77 ± 39 | 1116 ± 318 |
| 90 min[2] | 36 ± 3 | 891 ± 238 | 319 ± 91 | 2352 ± 441 |
| 2 hr | 46 ± 23 | 454 ± 79 | 257 ± 46 | 2983 ± 852 |
| 1.25 mg/kg/hr | | | | |
| Pre-Dose | 0 ± 0 | 0 ± 0 | 0 ± 0 | 0 ± 0 |
| 15 min | 0 ± 0 | 72 ± 15 | 13 ± 8 | 59 ± 24 |
| 30 min | 5 ± 2 | 63 ± 15 | 32 ± 12 | 121 ± 28 |
| 90 min | 9 ± 1 | 64 ± 14 | 65 ± 16 | 293 ± 73 |
| 2 hr | 3 ± 1 | 68 ± 11 | 38 ± 14 | 226 ± 64 |
| 4 hr | 12 ± 1 | 77 ± 8 | 30 ± 28 | 193 ± 127 |
| 6 hr | 0 ± 0 | 0 ± 0 | 0 ± 0 | 64 ± 10 |
| 8 hr | 15 ± 4 | 67 ± 29 | 6 ± 2 | 62 ± 26 |

Values are presented as the mean±SE of 4 values.
This was also the case for bile, but less so, while for urine the impact of the addition of phosphoric acid was variable.

Figure 2A:
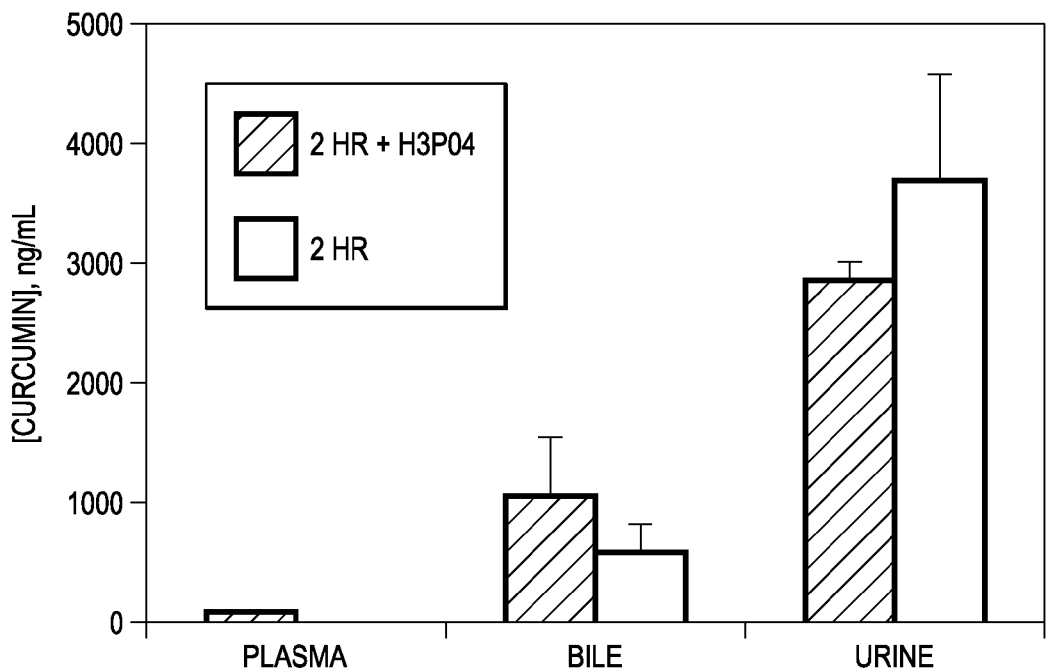
FIGS. 2A-2D are graphs of the plasma, bile and urine curcumin levels as a function of time after infusion.
Figure 2B:
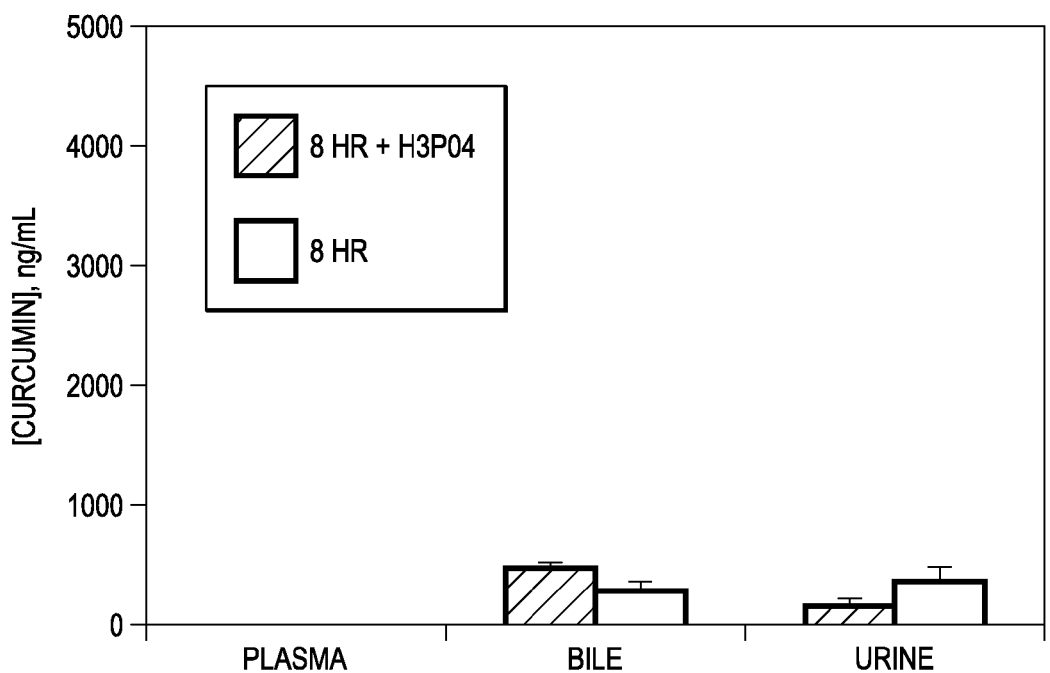
Figure 2C:
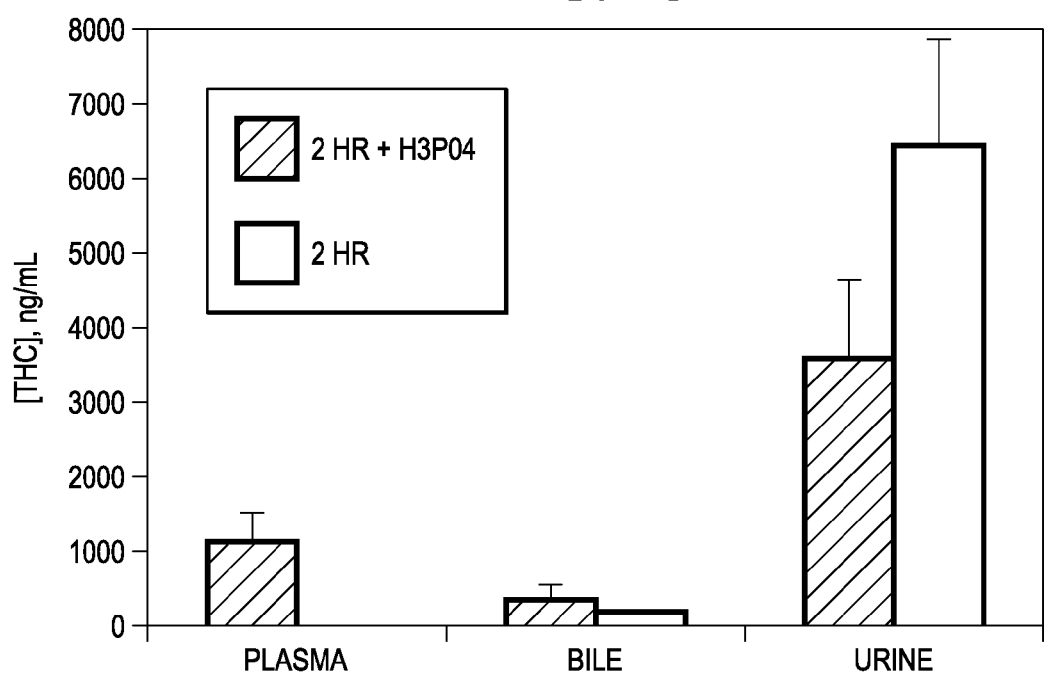
Figure 2D:
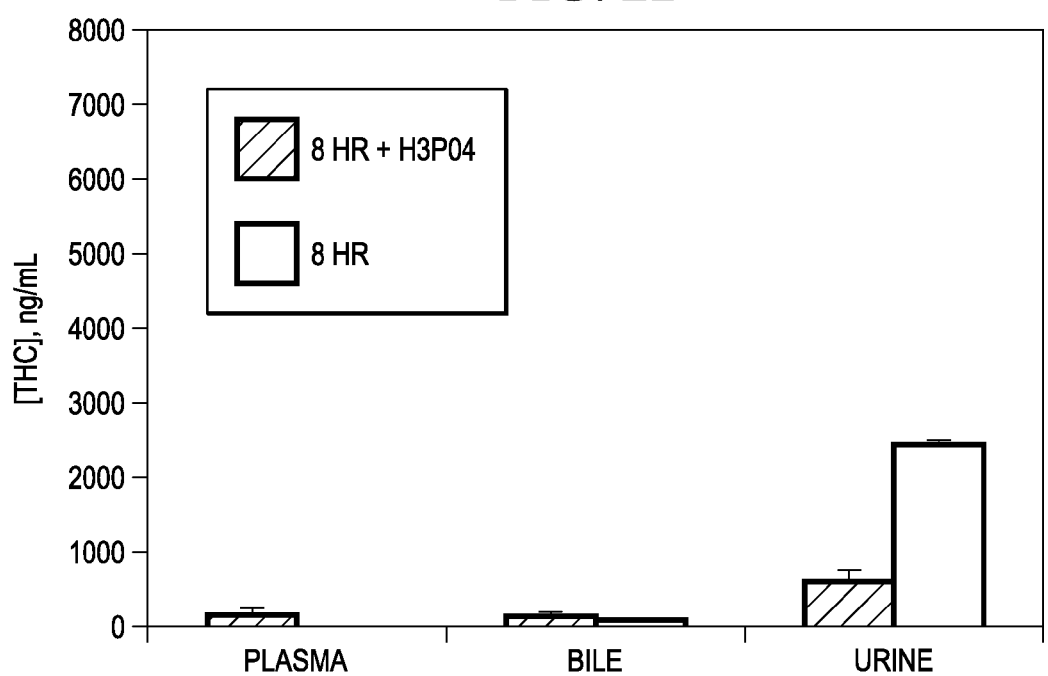

FIGS. 2A-2D are graphs of the plasma, bile, and urine curcumin post-infusion levels as a function of time after infusion plasma, bile, and urine levels. FIG. 2A is a graph of curcumin levels following a 2 hour infusion of 5 mg/kg/hr curcumin. FIG. 2B is a graph of curcumin levels following an 8 hour infusion of 1.25 mg/kg curcumin. FIG. 2C is a graph of THC levels following a 2 hour infusion of 5 mg/kg/hr curcumin. FIG. 2D is a graph of THC levels following an 8 hour infusion of 1.25 mg/kg/hr curcumin. Table 3 shows THC in the absence of phosphoric acid, the value is presented as the mean±SE of three determinations, otherwise all values are presented as the mean±standard error of 4 dogs.

Equivocal data for the bioanalysis of curcumin in the plasma of rats has been observed in the literature following oral administration of high doses [2]. Detection methods rather than plasma stability were speculated as the reason for the discrepancy, however, it appears that plasma/tissue stability would also be an issue in the bioanalysis of curcumin. One embodiment of the present invention provides the quantification of curcumin and THC stabilized by phosphoric acid in plasma, bile, and urine samples.

Upon a 2 hour infusion of curcumin at 5 mg/kg/hr (total dose 10 mg/kg), the plasma levels of curcumin rose to attain a maximum concentration of 320 ng/mL by 1.5 hours and then began to stabilize/fall during the infusion. Upon cessation of the infusion, there was a rapid drop in plasma concentrations of curcumin from 257 ng/mL to 65 ng/mL in 15 minutes. THC had a similar concentration-time profile. For the 8 hour infusion of curcumin at a rate of 1.25 mg/kg/hr (total dose 10 mg/kg), peak plasma concentrations of 187 ng/mL were also reached by 1.5 hours and then began to fall during the infusion period and thus, steady-state levels were not achieved; a similar concentration-time profile was also observed for THC. The ratio of THC to curcumin based on AUC was 9.6 for the 2 hour infusion and 6.3 for the 8 hour infusion. The drop in plasma levels of both curcumin and its metabolite, THC, upon the 8 hour infusion suggests that infusion of curcumin may activate or enhance its own elimination.

Computer assisted pharmacokinetic analysis of the plasma concentration data was only shown for the 2 hour infusion. The estimated PK parameters for curcumin and THC are shown in Table 4, while the $C_{max\ observed}$ and calculated AUC are shown in Table 2.

Table 4 below illustrates the estimated PK parameters of curcumin and THC. For a 2 hour intravenous infusion at a dose rate of 2 mg/kg/hr; total dose 10 mg/kg. The estimated PK parameters were determined by fitting the data to a first-order elimination continuous intravenous infusion model.

| Parameter | Units | Curcumin | THC |
|---|---|---|---|
| AUC | ng * hr/mL | 485 | 5185 |
| $C_{max}$ | ng/mL | 233 | 2429 |
| $t_{1/2(e)}$[1] | hr | 0.4 | 0.5 |
| $Ke$[1] | hr⁻¹ | 1.6 | 1.4 |
| MRT[1] | hr | 0.6 | 0.7 |
| CL | L/hr/kg | 20.6 | |
| Vss | L/kg | 12.7 | |

The rapid decrease in plasma concentration of curcumin is consistent with short $t_{1/2(e)}$ and MRT values of 0.4 and 0.6 hours respectively as a result of a high clearance of 20.6 L/kg/hr from a volume of distribution of 12.7 L/kg. The fitted $C_{max}$ and AUC values of 233 ng/mL and 485 ng*hr/mL are close to the observed $C_{max}$ of 320 ng/mL and calculated AUC of 394 ng*hr/mL. THC had estimated $t_{1/2(e)}$ and MRT values close to those of curcumin with the estimated values being 0.5 and 0.7 hours, respectively with $C_{max}$ and AUC values of 2429 ng/mL and 5185 ng*hr/mL, compared to the observed values of 2983 ng/mL and 3797 ng*hr/mL. The observed $C_{max}$ values for curcumin at infusion dose rates of 1.25 and 5.0 mg/kg/hr were close to being dose-proportional to the dosing rate, with dosing rate normalized $C_{max}$ values ($C_{max}$/Dosing rate in mg/kg/hr) of 64 and 53 ng/mL observed for the 2 and 8 hour infusions. The AUDs and infusion dose rate normalized AUDs up to 2 hours for the high and the low infusion rates were 354 and 82 ng*hr/mL and 59 and 66 ng*hr/mL, respectively, also consistent with dose-proportionality.

Measurement of the levels of curcumin and THC in the plasma, urine, and bile provide additional information concerning the disposition of curcumin (FIG. 2A-2D; Table 5 below). For bile, the levels of curcumin and THC were somewhat higher in female dogs compared to the male dogs. At both the high and low infusion rate of 1.25 mg/kg/hr, curcumin was found at higher concentrations in the urine and bile compared to plasma. At the low infusion rate, the urine and bile to plasma concentration ratios were 10 and 32, respectfully while at the higher infusion rate, the values observed were 44 and 16, respectfully.

Table 5 illustrates plasma, urine, and bile levels of curcumin and THC 15 minutes, 2 hours and 8 hours post infusion.

| Mattrix | 2 hour | 8 hour | 2 hour | 8 hour |
|---|---|---|---|---|
| | [Curcumin], ng/mL | | [Curcumin + $H_3PO_4$], ng/mL | |
| Plasma | 0 ± 0 | 0 ± 0 | 65 ± 28 | 14 ± 14[1] |
| Urine | 3657 ± 932 | 369 ± 247 | 2842 ± 170 | 148 ± 87 |
| Bile | 590 ± 224 | 292 ± 83 | 1028 ± 539 | 449 ± 96 |
| | [THC], ng/mL) | | [THC + $H_3PO_4$], (ng/mL) | |
| Plasma | 38 ± 4 | 20 ± 4[2] | 1167 ± 379 | 142 ± 122 |
| Urine | 6417 ± 1450 | 2451 ± 84 | 3587 ± 1083 | 621 ± 206 |
| Bile | 187 ± 74 | 84 ± 12 | 391 ± 197 | 168 ± 53 |

Unless indicated otherwise, values are the mean±SE of 4 determinations. Three values were 0 and one value was 58 ng/mL. Mean±SE of 3 determinations.

The liver and the kidney can eliminate curcumin from the plasma and at higher plasma concentrations the kidney can excrete more curcumin while biliary excretion is approaching saturation. This is consistent with studies in rats where tissue disposition studies of intravenously administered curcumin demonstrated the highest exposure in the liver and kidney [3]. Modulation of renal transporters may play an important role in the enhancement of the elimination of curcumin previously mentioned. For THC the urine to plasma concentration ratios were higher than the bile to plasma concentration ratios, both at the low and high infusion rates, with values of 3.1 and 4.4 compared to 0.3 and 1.2, respectively. This is consistent with metabolism of curcumin to THC by the hepatic and extrahepatic tissues, accumulation of THC in the plasma and excretion via the urine.

These data demonstrate drug stability, dose, and schedule of administration represent important and malleable components of curcumin clinical therapeutics. Tissue phenotype, metabolism, excretion routes, transport mechanisms and distribution are important but less subject to modification. Of these parameters curcumin degradation prior to and during analytic procedures is critically important and contributes to the variences and validity of plasma levels reported in animal studies of oral and parenteral curcumin administration. The high susceptibility to ambient light and pH of curcumin was resolved by the addition of phosphoric acid to stabilize curcumin prior to analytical processing.

Another factor contributing to misinformation regarding curcumin blood levels in animal models is the effect of metabolic activity. Curcumin can be released as free curcumin from any of the delivery vehicles, and distributes mainly to circulating and tissue lipids because of low aqueous solubility or is metabolized to a number of secondary compounds via conjugation with glucuronides or sulfates, or reduced to dihydrocurcumin, THC and octahydrocurcumin. Although the specific and collective biological activity of these metabolites in animal models has not been published. The predominant reduced metabolite is THC and has a similar biological activity to curcumin and can be converted by NADH-dependent dihydrocurcumin by intestinal *E. Coli*. THC can also be converted from curcumin via a specific enzyme reductase, which has a molecular mass of 82 KDa and consists of two identical subunits with a restricted substrate spectrum, preferentially acting on curcumin. Its mechanism of action on curcumin is rendered in two steps (i.e., two enzyme reactions). The first is a NADPH-dependent reduction to an intermediate dihydrocurcumin and the second is NADPH-dependent curcumin/dihydrocurcumin reductase to THC. The enzyme is part of the medium chain dehydrogenase-reductase superfamily, and its presence raises intriguing issues of enzyme origins and distribution. It is found in the blood of mice following intraperitoneal administration of curcumin, and it is assumed that the enzyme is also present in human blood and tissues: particularly the liver in humans. It is also found in a particular strain of human origin intestinal *E. coli*: K-12 substr. MG1655 version 15.1. While there are no published studies reporting on levels of this reducing enzyme in animal models, the significant presence of THC in the plasma of the dogs strongly suggests the presence of the enzyme in tissues and blood.

The addition of phosphoric acid to plasma and bile samples in dogs prevented the degradation of curcumin and THC, which raises issues of validity of published data on curcumin distribution and excretion. Infusion of liposomal curcumin (LIPOCURC™) in dogs at two different infusion rates resulted in higher plasma levels of curcumin and THC with a 2 hour infusion compared to an 8 hour infusion. The $C_{max}$ and $AUC_{2\,hr}$ normalized to the infusion dose rate were proportional. The plasma levels of THC were higher than curcumin with the ratio of plasma THC to curcumin ranging from 6.3-9.6. These data emphasize the putative presence of a curcumin reducing enzyme in blood or tissues.

Analysis of the 2 hour curcumin infusion data provided estimates of the plasma $t_{1/2(e)}$ and the mean residence times (MRT) which were short, ranging from 0.4-0.7 hours. The short plasma $t_{1/2(e)}$ and MRT are likely a consequence of the clearance of curcumin by both hepatic and renal routes. Clearances of curcumin and THC over 8 hours infusion are augmented, preventing attainment of a steady-state. The mechanism may potentially be through modulation of renal transporters. The present invention provides a 2 hour infusion of curcumin, THC or curcumin and THC would be preferable for liquid malignancies while the 8 hour infusion of curcumin, THC or curcumin and THC for solid tumors in the absence of tumor cell/tissue data.

In addition the present invention may be administered intravenously a therapeutically effective amount of a pharmaceutical composition curcumin, curcumin analogues, curcumin derivatives or combinations thereof dissolved or dispersed in a suitable aqueous or non-aqueous medium, wherein the curcumin is enclosed in one or more spherical liposomes or is conjugated to one or more biodegradable polymers. In another aspect the liposomes comprise a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In a specific aspect the one or more liposomes have a size of about 100 nm. In another aspect the therapeutically effective amount comprises 50 nM/kg of body weight of the subject. In yet another aspect the pharmaceutical composition is optionally administered along with related co-factors, proteins, antibodies, pain medications, and other pharmaceutically active agents. In another aspect of the method disclosed hereinabove the one or more pharmaceutically active agents are selected from the group consisting of L-dopa, Carbidopa, benserazide, Tolcapone, dopamine agonists bromocriptine, pergolide, pramipexole, ropinirole, piribedil, cabergoline, apomorphine, lisuride, MAO inhibitors, selegiline, and rasagiline.

In one aspect of the composition disclosed hereinabove the one or more spherical liposome or the polymer conjugate may be dispersed in a dispersion medium, wherein the dispersion medium is an aqueous or non-aqueous dispersion medium. In related aspects the lipid or the phospholipid is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate and the one or more biodegradable polymers are selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly (amino acids), copolymers, terpolymers, and combinations or mixtures thereof.

In another aspect the composition is administered intravenously, sub-cutaneously, intra-muscularly, or intra-peritoneally. In a specific aspect the one or more liposomes have a size of about 100 nm. In yet another aspect the composition is administered intravenously.

In another aspect the present invention may include lipid or the phospholipid selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In yet another aspect the composition is administered intravenously, sub-cutaneously, intra-muscularly or intra-peritoneally. In another aspect the one or more liposomes have a size of about 100 nm. In a specific aspect the composition is administered intravenously.

In specific aspects of the method described hereinabove the one or more liposomes have a size of about 100 nm and the therapeutically effective amount comprises 50 nM/kg of body weight of the subject. In a related aspect the pharmaceutical composition is optionally administered along with related co-factors, proteins, antibodies, pain medications, and other pharmaceutically active agents, wherein the pharmaceutically active agents comprise serotonin reuptake inhibitors sertraline and paroxetine.

Tissue concentration data arising from the infusion of liposomal curcumin in 8 (4 female and 4 male) Beagle dogs were used to assemble this report. The results and analysis are presented for 12 tissue samples (brain cortex, hippocampus, striatum, brain stem, heart, lungs, muscle, liver, kidney, pancreas, intestinal wall and urinary bladder) following the termination of intravenous infusion at a total dose of 10 mg/kg infused over a period of either 2 or 8 hours. Tissue levels of curcumin and its metabolite, tetrahydrocurcumin (THC) were measured in animals that were killed and subject to necropsy 15 minutes post-infusion to determine the tissue distribution and pharmacokinetics of curcumin and THC following two different rates of infusion and two different analyte preservation/stabilization methods (with and without $H_3PO_4$).

The test article will be administered to 8 Beagle dogs by intravenous infusion over two hours (Part A) or eight hours (Part B) as shown in Table 6.

TABLE 6

Summary of Treatment Groups

| Groups | Dose (mg/kg) | Concentration of Curcumin (mg/mL) | Infusion Rate mL/kg/hr | Duration of Infusion (hr) | Number of Beagle Dogs On Study[a] | |
|---|---|---|---|---|---|---|
| | | | | | M | F |
| 1. Part A, Liposomal Curcumin | 10 | 0.5 | 10 | 2 | 2 | 2 |
| 2. Part B, Liposomal Curcumin | 10 | 0.125 | 10 | 8 | 2 | 2 |

Fifteen minutes following either the 2 hour or 8 hour infusion, blood, urine and bile samples were taken, prior to the dogs being necropsied and organs removed for the isolation of tissues. Multiple samples of tissue weighing approximately 1 gram were removed and snap frozen in the presence or absence of phosphoric acid ($H_3PO_4$). For all tissue samples, the levels of curcumin and THC were determined using a method developed by the Bioanalytical Department at Nucro-Technics. Phosphoric acid was used to treat one set of samples based on preliminary studies indicating that phosphate increased the stability of curcumin and THC in the tissue matrix. Values that were below the limit of quantification were assigned a value of 0. As there were no consistent differences between the tissue levels of curcumin in males and female dogs, the average plasma concentrations from male and female dogs was used to assess the tissue distribution results. Tissue distribution data was analyzed using, unless stated, the data from 4 dogs and are presented as the mean±standard error (S.E.).

The distribution of curcumin and THC in tissues is illustrated in Tables 7-11. In general, curcumin and THC were widely distributed amongst the 12 tissues assessed. While in plasma the addition of phosphoric acid had a clear stabilizing effect on both the levels of curcumin and THC, the effects in tissues was less clear and to some extent tissue dependent and more evident for THC. Thus, despite the high degree of variability for some tissues, for brain tissue, phosphoric acid had a clear stabilizing effects, again more prominent for THC, while in other tissues, the stabilizing effect of phosphoric acid was minor or absent (i.e. heart and kidney). These differences may arise as a consequence of differing metabolic capabilities for each tissue.

TABLE 7

Tissue Distribution of Curcumin in the Presence and Absence of $H_3PO_4$ following 2 hour infusions.

| Tissue | Levels (ng/g)[1] | | | |
|---|---|---|---|---|
| | No $H_3PO_4$ | S.E. | Plus $H_3PO_4$ | S.E. |
| Cortex, Brain | 0.52 | 0.05 | 0.74 | 0.13 |
| Hippocampus | 0.09 | 0.00 | 0.09 | 0.09 |
| Striatum | 0.33 | 0.10 | 0.48 | 0.07 |
| Brain Stem | 0.30 | 0.04 | 0.45 | 0.06 |
| Heart | 0.49 | 0.08 | 0.48 | 0.09 |
| Lungs | 86.82 | 24.99 | 22.86 | 2.14 |
| Muscle | 1.23 | 0.32 | 0.19 | 0.02 |
| Liver | 4.28 | 1.90 | 1.82 | 0.45 |
| Kidney | 1.03 | 0.17 | 0.89 | 0.15 |
| Pancreas | 2.02 | 0.71 | 0.92 | 0.35 |
| Intestinal Wall | 2.97 | 0.98 | 1.14 | 0.26 |
| Urinary Bladder | 0.60 | 0.07 | 0.69 | 0.12 |

[1]Phosphate was added to the tissue samples in the form of phosphoric acid

TABLE 8

Tissue Distribution of THC in the Presence and Absence of $H_3PO_4$ following 2 hour infusions.

| Tissue | Levels (ng/g)[1] | | | |
|---|---|---|---|---|
| | No $H_3PO_4$ | S.E. | Plus $H_3PO_4$ | S.E. |
| Cortex, Brain | 0.68 | 0.05 | 3.08 | 0.30 |
| Hippocampus | 0.75 | 0.09 | 6.46 | 1.82 |
| Striatum | 6.22 | 3.10 | 11.12 | 1.42 |
| Brain Stem | 2.34 | 0.34 | 10.62 | 1.30 |
| Heart | 2.51 | 0.68 | 0.69 | 0.42 |
| Lungs | 24.99 | 5.11 | 2.14 | 2.67 |
| Muscle | 5.26 | 1.33 | 4.19 | 1.03 |
| Liver | 1.90 | 0.67 | 0.45 | 0.81 |
| Kidney | 3.06 | 0.63 | 4.25 | 0.61 |
| Pancreas | 2.02 | 0.71 | 0.92 | 0.35 |
| Intestinal Wall | 0.73 | 0.40 | 2.12 | 0.89 |
| Urinary Bladder | 0.84 | 0.20 | 0.87 | 0.34 |

[1]Phosphate was added to the tissue samples in the form of phosphoric acid.

TABLE 9

Tissue Distribution of Curcumin in the Presence and Absence of $H_3PO_4$ following 8 hour infusions.

| Tissue | Levels (ng/g)[1] | | | |
|---|---|---|---|---|
| | No $H_3PO_4$ | S.E. | Plus $H_3PO_4$ | S.E. |
| Cortex, Brain | 0.72 | 0.18 | 0.81 | 0.15 |
| Hippocampus | 0.00 | 0.00 | 0.01 | 0.01 |
| Striatum | 0.15 | 0.02 | 0.49 | 0.08 |
| Brain Stem | 0.41 | 0.10 | 0.58 | 0.04 |
| Heart | 0.67 | 0.15 | 0.75 | 0.17 |
| Lungs | 317.93 | 101.28 | 250.75 | 56.42 |
| Muscle | 3.25 | 1.31 | 0.79 | 0.24 |
| Liver | 39.38 | 13.70 | 28.38 | 10.30 |

TABLE 9-continued

Tissue Distribution of Curcumin in the Presence and Absence of $H_3PO_4$ following 8 hour infusions.

| Tissue | Levels (ng/g)[1] | | | |
|---|---|---|---|---|
| | No $H_3PO_4$ | S.E. | Plus $H_3PO_4$ | S.E. |
| Kidney | 2.71 | 0.65 | 2.77 | 1.04 |
| Pancreas | 1.88 | 0.62 | 2.84 | 0.76 |
| Intestinal Wall | 1.79 | 0.53 | 0.84 | 0.17 |
| Urinary Bladder | 3.24 | 1.37 | 2.26 | 0.51 |

[1]Phosphate was added to the tissue samples in the form of phosphoric acid.

TABLE 10

Tissue Distribution of THC in the Presence and Absence of $H_3PO_4$ following 8 hour infusions.

| Tissue | Levels (ng/g)[1] | | | |
|---|---|---|---|---|
| | No $H_3PO_4$ | S.E. | Plus $H_3PO_4$ | S.E. |
| Cortex, Brain | 0.06 | 0.04 | 0.49 | 0.12 |
| Hippocampus | 0.01 | 0.01 | 1.13 | 0.35 |
| Striatum | 1.12 | 0.11 | 3.14 | 0.26 |
| Brain Stem | 0.83 | 0.08 | 3.02 | 0.37 |
| Heart | 0.51 | 0.08 | 0.03 | 0.03 |
| Lungs | 10.81 | 2.50 | 6.36 | 2.13 |
| Muscle | 0.38 | 0.25 | 0.93 | 0.20 |
| Liver | 2.63 | 0.62 | 2.25 | 0.57 |
| Kidney | 1.32 | 0.18 | 2.04 | 0.32 |
| Pancreas | 0.34 | 0.19 | 1.34 | 0.52 |
| Intestinal Wall | 0.31 | 0.31 | 0.21 | 0.12 |
| Urinary Bladder | 1.37 | 0.42 | 1.11 | 0.41 |

[1]Phosphate was added to the tissue samples in the form of phosphoric acid

TABLE 11

$H_3PO_4$ stabilized Tissue Partition Coefficients (Kp) for Curcumin and THC following 2 hour and 8 hour infusions.

| Tissue | Kp [tissue]/[plasma][1] | | | |
|---|---|---|---|---|
| | Curcumin, 2 hr | THC, 2 hr | Curcumin, 8 hr | THC, 8 hr |
| Cortex, Brain | 0.0134 | 0.0006 | 0.0544 | 0.0047 |
| Hippocampus | 0.0016 | 0.0014 | 0.0007 | 0.0108 |
| Striatum | 0.0087 | 0.0039 | 0.0329 | 0.0300 |
| Brain Stem | 0.0081 | 0.0037 | 0.0389 | 0.0289 |
| Heart | 0.0087 | 0.0000 | 0.0503 | 0.0003 |
| Lungs | 0.4126 | 0.0078 | 16.8289 | 0.0609 |
| Muscle | 0.0034 | 0.0011 | 0.0530 | 0.0089 |
| Liver | 0.0329 | 0.0028 | 1.9047 | 0.0215 |
| Kidney | 0.0161 | 0.0025 | 0.1859 | 0.0195 |
| Pancreas | 0.0166 | 0.0017 | 0.1906 | 0.0128 |
| Intestinal Wall | 0.0206 | 0.0003 | 0.0564 | 0.0020 |
| Urinary Bladder | 0.0125 | 0.0014 | 0.1517 | 0.0106 |

[1]The plasma concentrations used to calculate the tissue partition coefficients were an average of the plasma concentration measured at the end of the infusion period and 15 minutes post infusion and were for 2 and 8 hours curcumin concentrations, 55.4 and 14.9 ng/mL, respectively and for 2 and 8 hours THC concentrations, 810.9 and 104.5 ng/mL, respectively.

For the purpose of consistency with the discussion of the plasma, bile and urine PK of curcumin and THC, the tissue distribution results will be discussed for tissue levels determined in the presence of phosphoric acid. Curcumin and THC were distributed in all of the tissues investigated to different extents. Following the 2 hours infusion, the tissue distribution was high for curcumin in the lung (22.86 ng/g) compared to other tissues (13-254-fold). The next highest tissue was the liver (1.82 ng/g), with distribution in other tissues ranging from 0.09-1.14 ng/g. The high distribution of curcumin into the lung may be due related to fact that it is a very lipophilic compound. A similar pattern was observed for THC following the 2 hour infusion, with comparable tissue levels of THC to curcumin observed.

Upon 8 hours of infusion, albeit at a lower infusion concentration, the extent of curcumin and THC changed. While the lung and liver again had the highest and second highest levels of curcumin, there were clearly increased concentrations of curcumin and THC in the liver and lungs with 2 hours versus 8 hours levels of 22.86 vs 250.75 ng/g and 1.82 vs 28.38 ng/mL, respectively. The highest level in the lung observed, 250.75 ng/g of curcumin translates into a tissue concentration of 0.68 µM accepting that 1 gram tissue is equivalent to 1 mL of volume. Curcumin levels ranged from 0.01-2.84 ng/g in other tissues. The levels of THC in the pancreas, kidney and urinary bladder were also increased following 8 hours of infusion, while other tissues were comparable to those observed with the 2 hour infusion. The levels of THC were also increased following 8 hours of infusion compared to 2 hours infusion. The increased tissue incorporation of curcumin in the lung and liver with 8 hours of infusion is consistent with the previously reported inability to achieve steady-state plasma levels of curcumin during 8 hours of infusion, further supporting an enhancement of tissue uptake during the course of infusion. A comparison of the tissue partition coefficients (Kp) further support this point and sheds additional light on the impact of short versus longer infusions of curcumin on tissue distribution in dogs (Tables 10-11). Firstly, both following 2 and 8 hours of infusion, the majority of the Kp values for curcumin and THC are below one, suggesting a poor tissue distribution of curcuminoids into tissues and consistent with the low oral bioavailability of curcumin. Low Kp values have also been observed in rodent studies and ranged from 0.06-0.25 in the rat. Exceptions to this are the liver and lung with >1 values of 1.9 and 16.8 respectively with 8 hours of infusion. Secondly, the Kp values are higher for curcumin than for THC, which to some extent makes sense with the lower lipophilicity of THC. Thirdly, the Kp values are higher amongst all tissues for both curcumin and THC following the 8 hour infusion compared to the 2 hour infusion. This latter point highly supports and enhancement of the tissue distribution of curcuminoids with longer infusion. In the literature, curcumin has been reported to inhibit the transporter mediated efflux of drugs from cells. At the mechanistic level, this may indeed explain the increased uptake of curcumin into tissues with a longer infusion and inability to attain steady-state plasma levels. Essentially, as infusion proceeds, curcumin levels build-up in tissues and begins to progressively inhibit efflux, resulting in greater tissue sequestration over time, the extent of which in any one tissue being dependent on the balance between uptake and efflux transporter activity. The higher levels of THC in tissues at 8 hours may be a consequence of the metabolism of the higher tissues levels of curcumin. Thus, in addition to the conclusions reached from analysis of the plasma levels of curcumin, the rapid clearance of curcumin from the circulation in addition to the impact of the liver and kidney, may also involve a number of tissues and be dependent on their balance of transporter mediated uptake and efflux. Curcumin and THC were distributed amongst all of the tissues investigated with very high levels compared to other tissues observed in the lung. The liver had the second highest levels. With 8 hour infusion, the tissue levels of curcumin in the lung and liver increased substantially compared to 2 hour infusion, with the pancreas, kidney and urinary bladder also displaying higher tissue levels. Tissue partition coefficients for curcumin and THC were higher for the 8 hour infusion compared to the 2 hour infusion, suggesting that prolonged infusion of curcumin may facilitate tissue distribution via a transporter-dependent mechanism.

TABLE 12

Effect of duration of a single dose: 10 mg/kg:
2 hours vs 8 hours intravenous curcumin infusion on
the ratio of tissue distribution of curcumin: THC in dogs.

| Concentration of THC | Concentration of curcumin | |
|---|---|---|
| A<br>2 h infusion ><br>8 h infusion | B<br>8 h infusion ><br>2 h infusion | C<br>8 h infusion =<br>2 h infusion |
| lung<br>intestinal wall<br>heart<br>muscle<br>bladder<br>spleen<br>liver<br>kidney<br>pancreas<br>brainstem<br>cortex<br>striatum<br>hippocampus | lung<br>muscle<br>spleen<br>liver<br>kidney<br>pancreas | intestinal wall<br>heart<br>bladder<br>brainstem<br>cortex<br>hippocampus<br>striatum |

As seen in Table 12 above: In column A the THC concentrations are higher in all 13 organs tested following a 2 hour infusion of liposomal curcumin compared to an 8 hour liposomal curcumin infusion. In column B the curcumin concentrations of following intravenous infusions of liposomal curcumin appear to be both tissue specific and time dependent. The longer infusion (8 hour) distributes preferably to 6 tissues. In column C the curcumin concentrations are not significantly different in the 2 hour and 8 hour infusions in 7 other tissues. Intertissue variance. Variance following infusions may be due to several causes: vascular supply, penetration, local tissue clearance/excretion, enzymatic reduction to THC from curcumin.

TABLE 13

Average $H_3PO_4$ stabilized tissue concentrations
(ng/gm) of curcumin and THC of 4 dogs 2 male and
2 female following 2 hour and 4 dogs following 8
hour infusions of 10 mg/kg liposomal curcumin.

| Tissue | Two hour infusion | | Eight hour infusion | |
|---|---|---|---|---|
| | Curcumin | THC | Curcumin | THC |
| Lung | 22.86 | 9.37 | 250.75 | 6.36 |
| Liver | 1.81 | 4.58 | 28.38 | 2.24 |
| Spleen | 0.075 | 1.60 | 22.90 | 0.42 |
| Pancreas | 0.85 | 0.91 | 2.84 | 1.34 |
| Kidney | 0.89 | 4.25 | 2.76 | 2.03 |
| Bladder | 0.66 | 2.25 | 0.87 | 1.11 |
| Heart | 0.47 | 0.68 | 0.74 | 0.03 |
| Intestinal wall | 1.14 | 2.11 | 1.11 | 0.09 |
| Muscle | 0.18 | 4.19 | 0.68 | 2.42 |
| Brainstem | 0.45 | 10.6 | 0.57 | 3.02 |
| Cortex | 0.73 | 3.08 | 0.80 | 0.49 |
| Striatum | 0.48 | 11.11 | 0.49 | 3.13 |
| Hippocampus | 0.09 | 6.46 | 0.01 | 1.12 |

Interpretation. The distribution of intravenous liposomal curcumin to various body tissues is not homogeneous, and it appears that the lung, liver and spleen either collect or retain significantly more curcumin than the remaining tissues. These data show the 8 hour infusion leads to significantly higher levels of curcumin in the lung, liver, spleen, pancreas, kidney, and muscle hypothetically due to low enzymatic reduction to THC or decreased clearance. In other tissues: muscle, bladder, heart, and intestinal wall there is no significant difference. Levels of THC are significantly reduced in all tissues receiving the 8 hour infusion. These data reflect the net result of the tissue dependent presence of reductive enzymes, the delivery of curcumin to the tissues leading to lesser amounts of THC and the pharmacokinetic profile of THC. The brain tissues are remarkably clear for supporting the presence of THC over curcumin, in this case prolonged infusion leads to greater clearance and lesser concentrations. The infusion duration does effect curcumin and THC metabolism, and may have to be taken into consideration when treating different tissue pathologies. For example, cerebral disorders may be better treated with brief infusions to achieve higher levels of THC, assuming THC is equally or better effective against brain based disorders than curcumin.

TABLE 14

$H_3PO_4$ stabilized vs Non-stabilized tissue analysis following a 2 hour infusion of Liposomal curcumin.

|  | Curcumin | | THC | |
| --- | --- | --- | --- | --- |
|  | $+H_3PO_4$ | $-H_3PO_4$ | $+H_3PO_4$ | $-H_3PO_4$ |
| Lung | 22.86 | 86.80 | 9.37 | 17.73 |
| Spleen | 0.07 | 0.48 | 1.60 | 1.35 |
| Liver | 1.81 | 4.28 | 4.58 | 2.41 |
| Pancreas | 0.85 | 2.81 | 0.91 | 2.01 |
| Brainstem | 0.45 | 0.32 | 10.60 | 2.33 |
| Cortex | 0.73 | 0.52 | 3.08 | 0.67 |
| Striatum | 0.48 | 0.32 | 11.11 | 6.21 |
| Hippocampus | 0.09 | 0.00 | 6.46 | 0.75 |

TABLE 15

$H_3PO_4$ stabilized vs non-stabilized tissue analysis following an 2 hour infusion of Liposomal curcumin.

|  | Curcumin | | THC | |
| --- | --- | --- | --- | --- |
|  | $+H_3PO_4$ | $-H_3PO_4$ | $+H_3PO_4$ | $-H_3PO_4$ |
| Lung | 250.75 | 317.90 | 6.36 | 10.81 |
| Spleen | 22.90 | 28.63 | 0.42 | 0.32 |
| Liver | 28.38 | 39.38 | 2.24 | 2.63 |
| Pancreas | 2.84 | 1.87 | 1.34 | 0.33 |
| Brainstem | 0.57 | 0.41 | 3.02 | 0.83 |
| Cortex | 0.80 | 0.72 | 0.49 | 0.12 |
| Striatum | 0.49 | 0.14 | 3.13 | 1.12 |
| Hippocampus | 0.01 | 0.00 | 1.12 | 0.01 |

Following the 2 hour infusion, with regard to curcumin, higher levels were achieved in the absence of phosphoric acid addition in the following tissues: lung, spleen, liver, pancreas, while higher levels in all brain tissues examined were observed with the addition of phosphoric acid. With regard to THC, all brain, spleen and liver levels were higher with the addition of phosphoric acid while lung and pancreas tissues were lower. The patterns in the 8 hour infusions (Table 15) were as follows: higher levels of curcumin were achieved in the absence of phosphoric acid in the following tissues: lung, spleen, liver, while the addition of phosphoric acid induced higher levels in the pancreas. There was no significant on the impact of phosphoric acid on curcumin levels in all brain tissues. Regarding THC levels, the addition of phosphoric acid increased THC levels in all brain, and pancreatic tissues. The absence of phosphoric acid addition was associated with higher THC levels in lung tissue, but had no incremental impact in other tissues.

Extrapolating to humans, and based upon the variances in THC formation, and specific tissue levels of curcumin and THC following 8 hour and 2 hour infusions of liposomal curcumin including the presence or absence of added phosphoric acid for stabilization, designing administration schedules may best be adapted for specific tissue pathologies in order to achieve optimum therapeutic results. In a 60 kg adult, 370 mg/M2 is equivalent to 10 mg/kg/dose. Converting 10 mg/kg dose in dogs to humans: x0.5=5.0 mg/kg/dose. Clinical applications: decision suggestions for either 2 hour or 8 hour or longer infusions of liposomal curcumin.

Lung disorders. Curcumin concentrations in the lung are higher in the 8 hour infusion, than in the 2 hour infusion, and levels are further elevated when analyzed in the presence of phosphoric acid. Curcumin may have therapeutic value in treating scleroderma, as it has already been shown to protect rats from lung fibrosis induced by a variety of agents. THC concentrations in the lung are higher after the 2 hour infusion than in the 8 hour infusion, and levels are lower when analyzed in the presence of phosphoric acid. Tetrahydrocurcumin has high anti-oxidant activity potency in three bioassay models, i.e. the linoleic acid auto-oxidation model, rabbit erythrocyte membrane ghost system, and rat liver microsome system implying that hydrogenation of curcuminoids increases anti-oxidant ability.

Liver disorders: Curcumin concentrations in the liver are higher in the 8 hour infusion than in the 2 hour infusion, and further elevated in the presence of phosphoric acid. THC concentrations in the liver are higher after the 2 hour infusion than the 8 hour infusion, and are increased in the presence of phosphoric acid. In the 8 hour infusion there was no advantage to adding phosphoric acid. Spleen disorders: Curcumin concentrations in the spleen are higher in the 8 hour infusion than in the 2 hour infusion, and further elevated in the presence of phosphoric acid. Curcumin increases sub G1 cell populations with strong apoptosis-inducing activity. THC concentrations in the spleen are higher after the 2 hour infusion. Treatment with THC induced autophagic cell death in human HL-60 promyelocytic leukemia cells by increasing autophage marker acidic vascular organelle formation. Flow cytometry also confirmed that THC treatment did not increase sub-G1 cell population. Western blot analysis showed that THC significantly down-regulated phosphatidylinositol 3-kinase/protein kinase B and mitogen-activated protein kinase signalings including decreasing the phosphorylation of mammalian target of rapamycin, glycogen synthase kinase $3\hat{1}^2$ and p70 ribosomal protein S6 kinase. Conclusion: these data demonstrated the anticancer efficacy of THC by inducing autophagy, and provide prevention of human leukemia. Myelofibrosis (MF) a significant disease burden: 85% of myelofibrosis patients present with splenomegaly and 60% to 80% of MF patients report spleen-related symptoms. In MF, splenomegaly of any degree is clinically relevant, and since the majority of patients with MF experience debilitating symptoms, appropriate treatment should be considered. Muscle disorders: Curcumin concentrations in muscle tissue are higher in the 8 hour infusion than in the 2 hour infusion. Pancreatic disorders: Curcumin concentrations in pancreatic disorders are higher in the 8 hour infusion than in the 2 hour infusion. THC concentrations are higher after the 2 hour infusion than after an 8 hour infusion. Kidney disorders: Curcumin concentrations in renal disorders are higher in the 8 hour infusion than in the 2 hour infusion. THC concentrations in the kidney are higher after a 2 hour infusion, than after an 8 hour infusion. Neural disorders: Curcumin in the Brainstem, Cortex, Striatum, and Hippocampus: either 2 hour or 8 hour infusions produce similar concentrations which are unchanged by phosphoric acid addition. Curcumin was effective in reducing amyloid plaque burden, insoluble beta-amyloid peptide.

In the Parkinson's disease model, depletion of dopamine (DA) and DOPAC (3,4-dihydroxy phenyl acetic acid)) occurs with increased monoamine oxidase (MAO-B) activity. Administration of curcumin (80 mg/kg i.p.) and tetrahydrocurcumin (60 mg/kg i.p.) significantly reversed the MPTP-induced depletion of DA and DOPAC. The MAO-B activity was also significantly inhibited by these compounds. Both curcumin and THC exert neuroprotection against MPTP induced neurotoxicity. THC compared with curcumin gavage leads to dramatically higher drug plasma levels, however resulting brain levels of parent compounds were similar. Levels in the Brainstem, Cortex, Striatum and Hippocampus are increased in the 2 hour infusion and further increased by phosphoric acid in both 2 hour and 8 hour infusions.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of determining a curcumin level in a biological sample comprising the steps of:
    obtaining the biological sample from a subject suspected of comprising a curcuminoid composition, wherein the biological sample is suspected of comprising a curcuminoid;
    adding a strong acid to the biological sample, wherein the strong acid composition is non-buffering; and
    detecting the amount of curcuminoid in the biological sample, wherein the non-buffering strong acid reduces the degradation of the curcuminoid in the biological sample.

2. The method of claim 1, wherein the biological sample is an in vitro sample.

3. The method of claim 1, wherein the biological sample is an aqueous sample, a supernatant sample, a tears sample, a sputum sample, a blood sample or a bile sample.

4. The method of claim 1, wherein the curcuminoid composition comprises curcumin and analogues and derivatives selected from curcumin; tetrahydrocurcumin; hexahydrocurcumin and hexahydrocurcuminol, curcumin glucuronide, and curcumin sulfate.

5. The method of claim 1, wherein the strong acid is selected from at least one of a phosphoric acid, an orthophosphoric acid, a phosphate salt, or a Na-phosphate.

6. The method of claim 1, wherein the curcuminoid composition further comprises a liposome, a phospholipid or a polymer composition to form an encapsulated curcuminoid composition.

7. The method of claim 6, wherein the liposome, the phospholipid or the polymer composition is selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoylphosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate; or wherein the polymer composition is selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof.

8. The method of claim 6, wherein the encapsulated curcuminoid composition has a size of 10-900 nm.

9. A method of analyzing a biological sample comprising the steps of:
- obtaining a biological sample from a subject;
- providing the biological sample comprising a curcumin composition;
- adding a phosphate composition to the biological sample, wherein the phosphate composition is non-buffering; and
- detecting the amount of curcuminoid in the sample, wherein the non-buffering phosphate composition reduces the degradation of the curcuminoid in the sample.

10. The method of claim 9, further comprising the step of analyzing at least one property of the curcumin in the sample selected from Area under the Curve (AUC), peak plasma concentration ($C_{max}$), elimination half-life ($t_{1/2(e)}$), elimination rate constant ($K_e$), mean residence time (MRT), Clearance (CL), volume of distribution at steady state (Vss).

11. The method of claim 9, wherein the sample is a blood sample or a bile sample.

12. The method of claim 9, wherein the curcumin composition is selected from curcumin, tetrahydrocurcumin, hexahydrocurcumin and hexahydrocurcuminol, curcumin glucuronide, and curcumin sulfate.

13. The method of claim 9, wherein the phosphate composition is a phosphoric acid.

14. A method of stabilizing a curcumin or tetrahydrocurcumin in a biological sample comprising the steps of:
- providing a curcumin or tetrahydrocurcumin to a subject;
- obtaining the biological sample from the subject, wherein the biological sample is suspected of comprising curcumin or tetrahydrocurcumin;
- adding a phosphate composition to the sample, wherein the phosphate composition is non-buffering and at least one of stabilizes or reduces the degradation of the curcumin in the sample; and
- determining the amount of curcumin or tertahydrocurcumin in the biological sample.

15. The method of claim 14, wherein the curcumin composition is selected from Curcumin, tetrahydrocurcumin, hexahydrocurcumin and hexahydrocurcuminol, curcumin glucuronide, and curcumin sulfate.

16. The method of claim 14, wherein the phosphate composition comprises a phosphoric acid, an orthophosphoric acid, a phosphate salt, or a Na-phosphate.

17. A method of stabilizing curcumin in a plasma sample or a bile sample against degradation during an analytical process comprising the steps of:
- obtaining the plasma or bile sample from a subject, wherein the plasma or bile sample is suspected of comprising curcumin, wherein the curcumin is selected from at least one of
- curcumin, tetrahydrocurcumin, hexahydrocurcumin and hexahydrocurcuminol, curcumin glucuronide, and curcumin sulfate,
- adding a phosphate composition to the plasma or bile sample, wherein the phosphate composition is non-buffering and is selected from a phosphoric acid, an orthophosphoric acid, a phosphate salt, or a Na-phosphate, and
- detecting the amount of curcuminoid in the plasma or bile sample, wherein the non-buffering phosphate composition reduces the degradation of the curcumin in the plasma or bile sample.

\* \* \* \* \*